ND states Patent [19]
Du et al.

[11] 4,450,272
[45] May 22, 1984

[54] ANTIATHEROSCLEROTIC 1-PIPERAZINE-THICARBOXAMIDES

[75] Inventors: Mila T. Du, Suffern, N.Y.; Robert G. Shepherd, Selbyville, Del.

[73] Assignee: American Cyanamid Company, Stamford, Conn.

[21] Appl. No.: 375,526

[22] Filed: May 6, 1982

[51] Int. Cl.³ .................. C07D 403/04; C07D 401/04; A61K 31/495
[52] U.S. Cl. .................................... 544/357; 544/363; 424/250
[58] Field of Search ................................ 544/357, 363

[56] References Cited

U.S. PATENT DOCUMENTS 2,519,715  8/1950  Stewart et al. ...................... 544/357
3,941,789  3/1976  Renth et al. ......................... 544/363

OTHER PUBLICATIONS

Conroy et al., J. Am. Pharm. Assoc. 43 625–628 (1954).

Primary Examiner—Mark L. Berch
Assistant Examiner—Chabi C. Kalita
Attorney, Agent, or Firm—Edward A. Conroy, Jr.; Jack W. Richards

[57] ABSTRACT

This disclosure describes 4-heteroaryl-1-piperazinethiocarboxamides useful in the treatment of atherosclerosis in mammals.

6 Claims, No Drawings

ANTIATHEROSCLEROTIC 1-PIPERAZINE-THICARBOXAMIDES

BACKGROUND OF THE INVENTION

This invention is concerned with organic compounds which are useful as pharmaceutical agents. The compounds of the present invention are 1-piperazinethiocarboxamides which are capable of ameliorating atherosclerosis in mammals. The invention further relates to novel 1-piperazinethiocarboxamides and methods for the chemical synthesis of these compounds. The invention also relates to pharmaceutical compositions for the utilization of these compounds in the treatment of disease in mammals. The invention contemplates methods for treating atherosclerosis in a mammal in a manner designed to prevent, arrest, or reverse the course of the disease.

The specific compounds of this invention are 4-heteroaryl-1-piperazinethiocarboxamides and this invention contemplates as novel compounds per se only certain types of 4-heteroaryl-1-piperazinethiocarboxamides which are not known in the art. Four 4-(2-pyrazinyl)-1-piperazinethiocarboxamides have been described (Chem. Abstr. 49, 384d and 11666b); however, there is no known report of antiatherosclerotic activity for these compounds.

Atherosclerosis is a form of arteriosclerosis characterized by lipid accumulation in and thickening of the arterial walls of both medium and large-sized arteries. Arterial walls are thereby weakened and the elasticity and effective internal size of the artery is decreased. Atherosclerosis is the most common cause of coronary artery disease and is of great medical importance since the occlusion of medium and large-sized arteries diminishes the supply of blood to vital organs such as the heart muscles and the brain. The sequelae to atherosclerosis include ischemic heart disease, heart failure, life-threatening arrythmias, senility and stroke.

The fact that cholesterol is a major component of atherosclerotic lesions or plaques has been known for more than 100 years. Various researchers have studied the role of cholesterol in lesion formation and development and also, more importantly, whether lesion formation can be prevented or lesion development arrested or reversed. Atheromatous lesions have now been shown [Adams, et al., Atherosclerosis, 13, 429 (1974)] to contain a greater quantity of esterified as opposed to unesterified cholesterol than the surrounding undiseased arterial wall. The intracellular esterification of cholesterol with fatty acids is catalyzed by the enzyme "Fatty acyl CoA:cholesterol acyl transferase" or ACAT and the accumulation and storage of cholesterol esters in the arterial wall is associated with increased activity of this enzyme [Hashimoto and Dayton, Atherosclerosis, 28, 447 (1977)]. In addition, cholesterol esters are removed from cells at a slower rate than unesterified cholesterol [Bondjers and Bjorkerud, Atherosclerosis, 15, 273 (1972) and 22, 379 (1975)]. Thus, inhibition of the ACAT enzyme would diminish the rate of cholesterol esterification, decrease the accumulation and storage of cholesterol esters in the arterial wall, and prevent or inhibit the formation and development of atheromatous lesions. The compounds of the present invention are very potent inhibitors of the ACAT enzyme. Thus, these compounds are useful for controlling and reducing the cholesterol ester content of mammalian arterial walls and decreasing the accumulation and storage of cholesterol in the arterial walls of mammals. Further, the compounds of this invention inhibit the formation or development of atherosclerotic lesions in mammals.

The evidence that hyperlipidemia is one of the factors involved in coronary heart disease is very impressive. A most important study carried out in Framingham, Mass. (Gordon and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis, et al., 1974).

We have now found that certain members of this class of compounds can safely and effectively lower serum lipids in warm-blooded animals. Such action on serum lipids is considered to be very useful in the treatment of atherosclerosis. For some time it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The compounds of this invention exhibit antiatherosclerotic activity and the invention should not be construed as limited to any particular mechanism of antiatherosclerotic action.

SUMMARY OF THE INVENTION

This invention relates to new organic compounds, their preparation, pharmaceutical compositions containing them and their use in the treatment of atherosclerosis. More particularly, it is concerned with novel 1-piperazinethiocarboxamides which may be represented by the formula:

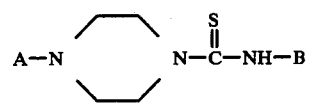

wherein A is selected from the group consisting of pyrazinyl, quinolyl, and methoxypyrazinyl and B is selected from the group consisting of cycloalkyl, benzyl, phenethyl, and phenyl substituted with at least one substituent selected from the group consisting of $C_1-C_4$ carboalkoxy, carboxy, and cyano.

This invention is further concerned with methods for treating atherosclerosis in a mammal with 1-piperazinethiocarboxamides which may be represented by the formula:

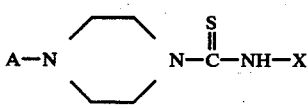

wherein A is selected from the group consisting of pyrazinyl, quinolyl, and methoxypyrazinyl and X is selected from the group consisting of $C_1$-$C_4$ alkyl, cycloalkyl, benzyl, phenethyl, phenyl, and phenyl substituted with at least one substituent selected from the group consisting of $C_1$-$C_4$ alkyl, $C_1$-$C_4$ alkoxy, halo, $C_1$-$C_4$ carboalkoxy, carboxy, and cyano.

This invention also relates to a method of reducing the cholesterol content of the arterial walls of mammals which comprises administering to said mammal an effective amount of a compound of formula II above.

This invention also relates to a method of treating hyperlipidemia in a mammal which comprises administering to said mammal an effective amount of a compound of formula II above.

This invention also relates to a method of inhibiting atherosclerotic lesion development in a mammal which comprises administering to said mammal an effective amount of a compound of formula II above.

This invention still further relates to a pharmaceutical composition which comprises an effective antiatherosclerotic amount of a compound of formula II above in association with a pharmaceutically acceptable carrier.

Finally, this invention relates to chemical processes for preparing the novel compounds of formula I above. These processes are disclosed more completely in the detailed description of the invention below.

Preferred embodiments of the invention involve compounds of formula I in which A is a 2-pyrazinyl group. More preferred embodiments involve compounds of formula I in which A is a 2-pyrazinyl group and B is a substituted phenyl group. The most preferred embodiments involve compounds of formula I in which A is a 2-pyrazinyl group and B is a phenyl group substituted with one cyano group. Specific preferred embodiments of the invention involve the compound 4'-cyano-4-(2-pyrazinyl)-1-piperazinethiocarboxanilide.

DETAILED DESCRIPTION OF THE INVENTION

The novel compounds of this invention represented by formula I may be prepared by reactions of piperazines of formula III in which A is as defined above with isothiocyanates of formula IV in which B is as defined above.

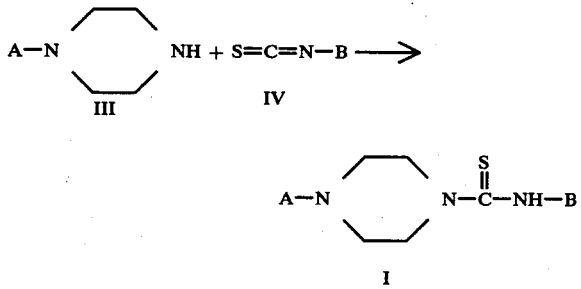

These reactions may be conducted in organic solvents such as ether, tetrahydrofuran, and methylene chloride at temperatures of from room temperature or below up to the boiling point of the solvent used and for reactions times of up to 24 hours or more. The resulting 1-piperazinethiocarboxamides of formula I are then isolated either by filtration or evaporation and purified by distillation under reduced pressure or by recrystallization from organic solvents such as ethanol, acetone, and benzene. An example of this process if the reaction of 1-(2-pyrazinyl)piperazine with 4-(cyanophenyl)isothiocyanate to yield 4'-cyano-4-(2-pyrazinyl)-1-piperazinethiocarboxanilide.

The 1-piperazinethiocarboxamides of the present invention are obtained as crystalline solids or distillable liquids. They are characterized by distinct melting or boiling points and unique spectra. They are appreciably soluble in organic solvents but generally less soluble in water. The preparation and properties of the compounds of this invention will be described in greater detail in conjunction with the examples shown below.

The compounds of this invention were assayed for three types of biological activity related to their potential use as antiatherosclerotic agents.

Compounds were tested for their ability to inhibit ACAT according to the following procedure:

Rat adrenals were homogenized in 0.2 M monobasic potassium phosphate buffer, pH 7.4, and centrifuged at 1000 times gravity for 15 minutes at 5° C. The supernatant, containing the microsomal fraction, served as the source of the cholesterol-esterifying enzyme, fatty acyl CoA:cholesterol acyl transferase (ACAT). A mixture comprising 50 parts of adrenal supernatant, 10 parts of albumin (BSA) (50 mg./ml.), 3 parts of test compound (final concentration 5.2 μg./ml.) and 500 parts of buffer was preincubated at 37° C. for 10 minutes. After treatment with 20 parts of oleoyl CoA ($^{14}$C —0.4 μCi) the mixture was incubated at 37° C. for 10 minutes. A control mixture, omitting the test compound, was prepared and treated in the same manner. The lipids from the incubation mixture were extracted into an organic solvent and separated by thin-layer chromatography. The cholesterol ester fraction was counted in a scintillation counter. This procedure is a modification of that described by Hashimoto, et. al., Life Scie., 12 (Part II), 1-12 (1973).

Compounds which produce a statistically significant inhibition of the ACAT enzyme are considered to be active.

The results of this test on representative compounds of this invention appear in Table I.

TABLE I

| Compound | % Inhibition |
|---|---|
| N—Phenethyl-4-(2-pyrazinyl)-1-piperazinethiocarboxamide | 33 |
| 4'-Isopropyl-4-(2-pyrazinyl)-1-piperazinethiocarboxanilide | 56 |
| N—Cyclohexyl-4-(2-pyrazinyl)-1-piperazinethiocarboxamide | 31 |
| 4'-Chloro-4-(2-pyrazinyl)-1-piperazinethiocarboxanilide | 31 |
| N—Ethyl-4-(2-quinolyl)-1-piperazinethiocarboxamide | 48 |
| N—Ethyl-4-(6-methoxy-2-pyrazinyl)-1-piperazinecarboxamide | 40 |

The compounds were also tested for their ability to lower lipid levels in mammals. The compounds were administered orally admixed with diet to groups of four male rats COBS, CD, SD strain from Charles River Breeding Laboratories, Inc., Wilmington, Mass. A control group of eight rats was maintained on the diet alone; test groups were maintained on the diet plus the indicated percentage of test compound by weight. After 5 days treatment, serum cholesterol and triglyceride concentrations were determined by direct enzymatic procedures using a Centrifichem ® System 400 autoanalyzer (Union Carbide Co.). Cholesterol concentrations were determined by the combined cholesterol esterase-cholesterol oxidase procedure of Roelschlau et. al., Zeit. Klin. Chem. Klin. Biochem., 12, 226 (1974). Triglycerides were determined by the combined method of lipase catalyzed hydrolysis of triglycerides to glycerol and free fatty acids [Bucolo, G. and David, H., Clin. Chem., 19, 476 (1973) and Wahlefeld, A. W., in "Methods of Enzymatic Analysis", Vol. 4, Bergmeyer, H. U., Editor, Academic Press, New York, N.Y. (1974), pp. 1831-1835] and the enzymatic oxidation of the glycerol which leads to the production of colored formazan [Stavropoulos, W. S. and Crouch, R. D., Clin. Chem., 20, No. 7, 857 (1974)]. Changes in serum lipids are expressed as percent lowering from the values in control animals which did not receive drug treatment. Compounds which produce statistically significant lowering of either sterol or triglycerides are considered to be active. The results of this test on representative compounds appear in Table II.

active. The results of this test on representative compounds of this invention appear in Table III.

TABLE III

| Compound | Result |
| --- | --- |
| N—Methyl-4-(2-pyrazinyl)-1-piperazine-thiocarboxamide | Active |
| 4'-Cyano-4-(2-pyrazinyl)-1-piperazine-thiocarboxanilide | Active |
| N—Phenyl-4-(2-pyrazinyl)-1-piperazine-thiocarboxamide | Active |
| N—Ethyl-4-(2-pyrazinyl)-1-piperazine-thiocarboxamide | Active |

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These

TABLE II

| Compound | % Compound in Diet | % Lowering of Serum Sterol | % Lowering of Serum Triglycerides |
| --- | --- | --- | --- |
| N—Methyl-4-(2-pyrazinyl)-1-piperazinethiocarboxamide | 0.1 | — | 31 |
| 4'-Cyano-4-(2-pyrazinyl)-1-piperazinethiocarboxanilide | 0.1 | — | 55 |
| N—Phenethyl-4-(2-pyrazinyl)-1-piperazinethiocarboxamide | 0.1 | 16 | — |
| N—Phenyl-4-(2-pyrazinyl)-1-piperazinethiocarboxamide | 0.1 | — | 52 |
| 2',6'-Dichloro-4-(2-pyrazinyl)-1-piperazinethiocarboxanilide | 0.1 | — | 37 |
| 2'-Chloro-4-(2-pyrazinyl)-1-piperazinethiocarboxanilide | 0.1 | — | 49 |
| 2'-Fluoro-4-(2-pyrazinyl)-1-piperazinecarboxanilide | 0.1 | — | 21 |
| N—Cyclohexyl-4-(2-pyrazinyl)-1-piperazinethiocarboxamide | 0.1 | — | 43 |
| 4'-Chloro-4-(2-pyrazinyl)-1-piperazinethiocarboxanilide | 0.1 | — | 49 |
| 4'-Fluoro-4-(2-pyrazinyl)-1-piperazinethiocarboxanilide | 0.1 | — | 37 |
| N—Ethyl-4-(6-methoxy-2-pyrazinyl)-1-piperazinecarboxamide | 0.1 | — | 38 |

The compounds were further tested for their ability to decrease aortic sterol content without effecting serum sterol.

Day-old-cockerels were placed on diets consisting of pullet starter mash supplemented with either 20 g. cholesterol (control group) or 20 g. cholesterol and 525 mg. test compound (drug-treated group) per kg. of diet.

For the control diet 20 g. of cholesterol is dissolved in 200 ml. of chloroform, mixed into one kg. of pullet starter mash and then the chloroform is removed by evaporation.

For the drug-treatment group 525 mg. of the test compound is dissolved in 100 ml. of chloroform, mixed into a diet prepared as described above and then the chloroform is evaporated.

The cockerels were housed three per cage and given water and their respective diet ad libitum for 14 days. Blood was collected by cardiac puncture and the serum was saponified [Trinder, P., Analyst, 77, 321 (1952)] and extracted and the cholesterol content determined [Zlatkis, A. et. al., J. Lab. Clin. Med., 41, 486 (1953)]. The aortae were removed, cleaned of adventitial tissue and the sterol content determined according to the above procedures. Compounds which produce statistically significant decreases in the aortic sterol content without having an effect on serum sterol are considered to be pharmaceutical preparations may contain, for example, from about 0.5% up to about 90% of the active ingredient in combination with the carrier, more usually between 5% and 60% by weight.

The antiatherosclerotic effective dosage of active ingredient employed may vary depending on the particular compound employed, the mode of administration and the severity of the condition being treated. However, in general, satisfactory results are obtained when the compounds of the invention are administered at a daily dosage of from about 2 milligrams to about 500 milligrams per kilogram of animal body weight, preferably given in divided doses two to four times a day, or in sustained release form. For most large mammals, the total daily dosage is from about 100 milligrams to about 5,000 milligrams preferably from about 100 milligrams to 2,000 milligrams. Dosage forms suitable for internal use comprise from about 25 to 500 milligrams of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agent, preserving agents, and antioxidants eg. vitamin E, ascorbic acid, BHT and BHA.

The preferred pharmaceutical compositions from the stand-point of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be more fully described in conjunction with the following specific examples which are not to be construed as limiting the scope of the invention.

EXAMPLE 1

N-Methyl-4-(2-pyrazinyl)-1-piperazinethiocarboxamide

To a solution of 6.56 g. of 1-(2-pyrazinyl)piperazine (U.S. Pat. No. 2,606,906) in 40 ml. of anhydrous ether is added a solution of 2.92 g. of methyl isothiocyanate in 40 ml. of anhydrous ether, dropwise over a period of 10 minutes. This suspension is stirred for one hour and the solid is collected and washed. This solid is dissolved in a mixture of 200 ml. of benzene and 50 ml. of ethanol with heat and then cooled to room temperature over 48 hours. The resulting solid is dissolved in 400 ml. of ethanol:ethyl acetate (1:3), concentrated to 200 ml. and chilled. The resulting solid is collected giving 4.34 g. of the desired product as white crystals, m.p. 197°–200° C.

EXAMPLE 2

4'-Cyano-4-(2-pyrazinyl)-1-piperazinethiocarboxanilide

To a solution of 4.92 g. of 1-(2-pyrazinyl)piperazine in 45 ml. of anhydrous ether is added a slurry of 4.8 g. of p-cyanophenyl isothiocyanate in 45 ml. of anhydrous ether, dropwise over 10 minutes. The mixture is stirred for 30 minutes and the resulting solid collected. This solid is dissolved in a mixture of 200 ml. of benzene and 200 ml. of ethanol and then cooled. The resulting solid is collected giving 6.95 g. of the desired product, m.p. 208°–210° C.

EXAMPLE 3

N-Phenethyl-4-(2-pyrazinyl)-1-piperazinethiocarboxamide

To a solution of 4.92 g. of 1-(2-pyrazinyl)piperazine in 30 ml. of anhydrous ether is added dropwise a solution of 4.89 g. of phenethyl isothiocyanate in 30 ml. of anhydrous ether over 10 minutes. An additional 30 ml. of anhydrous ether is required to maintain stirring over 30 minutes. The resulting solid is collected, dissolved in 100 ml. of benzene and 25 ml. of ethanol and cooled. The resulting solid is collected, giving 5.68 g. of the desired product as a white solid, m.p. 162°–163° C.

EXAMPLE 4

2',6'-Dichloro-4-(2-pyrazinyl)-1-piperazinethiocarboxanilide

To a solution of 4.92 g. of 1-(2-pyrazinyl)piperazine in 50 ml. of anhydrous ether is added dropwise a solution of 6.12 g. of 2,6-dichlorophenyl isothiocyanate in 50 ml. of anhydrous ether over 10 minutes. The mixture is stirred for 15 minutes and the resulting solid collected. This solid is dissolved with heat in a mixture of 200 ml. of acetone and 150 ml. of methanol and then cooled. The resulting solid is collected giving 5.29 g. of the desired product as white crystals, m.p. 225°–227° C.

EXAMPLE 5

2'-Chloro-4-(2-pyrazinyl)-1-piperazinethiocarboxanilide

To a solution of 4.92 g. of 1-(2-pyrazinyl)piperazine in 50 ml. of anhydrous ether is added dropwise a solution of 5.08 g. of 2-chlorophenyl isothiocyanate in 50 ml. of anhydrous ether over 5 minutes. The mixture is stirred for 30 minutes and the resulting solid is collected. This solid is recrystallized from 430 ml. of ethanol giving 7.41 g. of the desired product, m.p. 167°–169° C.

EXAMPLE 6

4-Isopropyl-4-(2-pyrazinyl)-1-piperazinethiocarboxanilide

To a solution of 4.92 g. of 1-(2-pyrazinyl)piperazine in 50 ml. of anhydrous ether is added dropwise a solution of 5.31 g. of 4-isopropylphenyl isothiocyanate in 50 ml. of anhydrous ether over 5 minutes. The mixture is stirred for 30 minutes and the resulting solid is collected and recrystallized from 150 ml. of ethanol, giving 9.31 g. of the desired product as white crystals, m.p. 167°–171° C.

EXAMPLE 7

N-Cyclohexyl-4-(2-pyrazinyl)-1-piperazinethiocarboxamide

To a solution of 4.92 g. of 1-(2-pyrazinyl)piperazine in 50 ml. of anhydrous ether is added dropwise a solution of 4.2 g. of cyclohexyl isothiocyanate in 50 ml. of anhydrous ether over 5 minutes. The mixture is stirred for 35 minutes and the resulting solid is collected and recrystallized from 50 ml. of ethanol, giving 7.58 g. of the desired product, m.p. 176°–178° C.

EXAMPLE 8

4'-Chloro-4-(2-pyrazinyl)-1-piperazinethiocarboxanilide

To a solution of 4.92 g. of 1-(2-pyrazinyl)piperazine in 50 ml. of anhydrous ether is added dropwise a solution of 5.08 g. of 4-chlorophenyl isothiocyanate in 50 ml. of anhydrous ether over a period of 5 minutes. The mixture is stirred for 30 minutes and the resulting solid is collected and recrystallized from 550 ml. of ethanol, giving 7.92 g. of the desired product as white crystals, m.p. 208°–210° C.

EXAMPLE 9

4'-Fluoro-(2-pyrazinyl)-1-piperazinethiocarboxanilide

To a solution of 4.92 g. of 1-(2-pyrazinyl)piperazine in 50 ml. of anhydrous ether is added dropwise a solution of 4.59 g. of 4-fluorophenyl isothiocyanate in 50 ml. of anhydrous ether with stirring. Stirring is continued for 30 minutes and the resulting solid is collected. This solid is dissolved in a mixture of 200 ml. of ethanol, and 75 ml. of acetone with heat, then concentrated to 200 ml. and cooled giving 7.43 g. of the desired product as a white solid, m.p. 195°–197° C.

EXAMPLE 10

N-Ethyl-4-(2-quinolyl)-1-piperazinethiocarboxamide

A mixture of 20.7 g. of 2-chloroquinoline, 15 g. of anhydrous piperazine, 15 g. of powdered sodium carbonate and 30 ml. of anhydrous ethanol is stirred and refluxed for 8 hours in a flask equipped with a Dean-Stark trap condenser. The mixture is diluted with 100 ml. of chloroform and filtered. The filtrate is extracted twice with water, dried over magnesium sulfate, filtered and the filtrate concentrated in vacuo to a brown semi-liquid. A 200 ml. portion of chloroform is added and the mixture is filtered. The filtrate is extracted with four 10 ml. portions of 3 N hydrochloric acid. The extracts are combined and the chloroform layer is saved. The aqueous layer is made basic with 10 N sodium hydroxide to pH 13 and then extracted with three 50 ml. portions of chloroform. The chloroform extracts are combined, washed with two 5 ml. portions of water, dried and concentrated in vacuo to a solid. This solid is dissolved in 30 ml. of methanol and filtered. To the filtrate is added 60 ml. of water. The resulting solid is collected and dried, giving 16.69 g. of 1-(2-quinolinyl)piperazine.

To a slurry of 4.26 g. of 1-(2-quinolinyl)piperazine in 30 ml. of anhydrous ether is added dropwise a solution of 1.74 g. of ethyl isothiocyanate in 30 ml. of anhydrous ether. The mixture is stirred for one hour and the resulting solid is collected and recrystallized from 150 ml. of ethanol, giving 4.43 g. of the desired product as a white crystalline solid, m.p. 193°–195° C.

EXAMPLE 11

N-Ethyl-4-(6-methoxy-2-pyrazinyl)-1-piperazinethiocarboxamide

A mixture of 29.8 g. of 2,6-dichloropyrazine, 17.2 g. of piperazine and 200 ml. of acetone is refluxed on a steam bath for 2 hours, then cooled and the resulting solid is collected, dried and recrystallized from 80% ethanol, giving 26.0 g. of 1-[2-(6-chloropyrazinyl)]-piperazine hydrochloride.

A mixture of 9.4 g. of 1-[2-(6-chloropyrazinyl)]-piperazine hydrochloride, 4.4 g. of sodium methoxide and 120 ml. of methanol is refluxed for 19 hours, cooled and diluted with 120 ml. of water. The mixture is extracted with four 25 ml. portions of chloroform which are combined, dried and concentrated in vacuo to a residue. This residue is dissolved in 50 ml. of methanol, 2.2 g. of sodium methoxide are added and the mixture is refluxed overnight, cooled and 50 ml. of water are added. This mixture is extracted with four 20 ml. portions chloroform, dried and evaporated to a yellow oil. This oil is redissolved in 50 ml. of methanol and a solution of 2.2 g. of sodium methoxide in 20 ml. of methanol is added. This mixture is refluxed 40 hours, diluted with 50 ml. of water and extracted with two 30 ml. portions of chloroform. The extracts are combined, dried and concentrated to dryness giving 6.78 g. of 1-(6-methoxypyrazinyl)piperazine as a yellow oil.

To a solution of 1.94 g. of 1-(6-methoxypyrazinyl)piperazine in 25 ml. of anhydrous ether is added dropwise a solution of 0.87 g. of ethylisothiocyanate in 25 ml. of anhydrous ether. The mixture is stirred 30 minutes and the solid collected and recrystallized from 80% ethanol, giving 2.27 g. of the desired product as white crystals, m.p. 120°–122° C.

EXAMPLE 12

2'-Fluoro-4-(2-pyrazinyl)-1-piperazinethiocarboxanilide

To a solution of 4.92 g. of 1-(2-pyrazinyl)piperazine in 50 ml. of anhydrous ether is added a solution of 4.59 g. of 2-fluorophenyl isothiocyanate in 50 ml. of anhydrous ether over a period of 10 minutes. The mixture is stirred for 30 minutes and the resulting solid is collected and then recrystallized from 200 ml. of ethanol, giving 7.04 g. of the desired product, m.p. 151°–153° C.

EXAMPLE 13

N-Butyl-4-(2-pyrazinyl)-1-piperazinethiocarboxamide

To a solution of 4.92 g. of 1-(2-pyrazinyl)piperazine in 80 ml. of anhydrous ether is added a solution of 3.45 g. of n-butyl isothiocyanate in 50 ml. of anhydrous ether, dropwise during 5 minutes. The mixture is stirred for 30 minutes and the resulting solid is collected and dissolved in 50 ml. of ethanol. Cooling and the addition of 2 ml. of water gives 4.96 g. of the desired product as white crystals, m.p. 97.5°–98.5° C.

EXAMPLE 14

N-tert-Butyl-4-(2-pyrazinyl)-1-piperazinethiocarboxamide

To a solution of 4.92 g. of 1-(2-pyrazinyl)piperazine in 50 ml. of anhydrous ether is added a solution of 3.45 g. of tert-butyl isothiocyanate in 50 ml. of anhydrous ether. The mixture is stirred for 30 minutes and the resulting solid is collected and recrystallized from 50 ml. of ethanol, giving 5.85 g. of the desired product as white crystals, m.p. 153°–156° C.

We claim:

1. A compound of the formula:

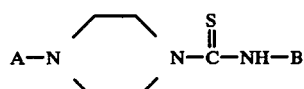

wherein A is selected from the group consisting of pyrazinyl, quinolyl, and methoxypyrazinyl and B is selected from the group consisting of, benzyl, phenethyl, and phenyl substituted with at least one substituent selected from the group consisting of $C_1$–$C_4$ carboalkoxy, carboxy, and cyano.

2. A compound as recited in claim 1, wherein A is a 2-pyrazinyl group.

3. A compound as recited in claim 2, wherein B is a phenyl group substituted with at least one substituent selected from the group consisting of $C_1$–$C_4$ carboalkoxy, carboxy, and cyano.

4. A compound as recited in claim 3, wherein B is a phenyl group substituted with one cyano group.

5. The compound as recited in claim 1, 4'-cyano-4-(2-pyrazinyl)-1-piperazinethiocarboxanilide.

6. The compound as recited in claim 1, N-phenethyl-4-(2-pyrazinyl)-1-piperazinethiocarboxamide.

* * * * *